(12) United States Patent
Balch et al.

(10) Patent No.: US 6,296,749 B1
(45) Date of Patent: *Oct. 2, 2001

(54) SYSTEM AND METHOD FOR CHROMATOGRAPHY AND ELECTROPHORESIS USING CIRCULAR OPTICAL SCANNING

(75) Inventors: Joseph W. Balch, Livermore; Laurence R. Brewer, Oakland; James C. Davidson, Livermore; Joseph R. Kimbrough, Pleasanton, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/290,445

(22) Filed: Apr. 13, 1999

(51) Int. Cl.[7] ............... G01N 27/26; G01N 27/447; G01N 21/00; G01N 21/64
(52) U.S. Cl. .................. 204/452; 204/450; 204/600; 204/603; 436/172; 250/458.1; 250/459.1; 250/461.1; 356/344
(58) Field of Search ................... 204/600, 603, 204/450, 452; 356/344; 250/458.1, 459.1, 461.1, 461.2; 422/165, 172

(56) References Cited

U.S. PATENT DOCUMENTS 5,483,075 * 1/1996 Smith et al. ............... 356/344 X 6,100,535 * 8/2000 Mathies et al. .............. 250/458.1

FOREIGN PATENT DOCUMENTS

WO 00/62043 * 10/2000 (WO).

* cited by examiner

Primary Examiner—Jill Warden
Assistant Examiner—John S. Starsiak, Jr.
(74) Attorney, Agent, or Firm—Eddie E. Scott; Alan H. Thompson

(57) ABSTRACT

A system and method is disclosed for chromatography and electrophoresis using circular optical scanning. One or more rectangular microchannel plates or radial microchannel plates has a set of analysis channels for insertion of molecular samples. One or more scanning devices repeatedly pass over the analysis channels in one direction at a predetermined rotational velocity and with a predetermined rotational radius. The rotational radius may be dynamically varied so as to monitor the molecular sample at various positions along a analysis channel. Sample loading robots may also be used to input molecular samples into the analysis channels. Radial microchannel plates are built from a substrate whose analysis channels are disposed at a non-parallel angle with respect to each other. A first step in the method accesses either a rectangular or radial microchannel plate, having a set of analysis channels, and second step passes a scanning device repeatedly in one direction over the analysis channels. As a third step, the scanning device is passed over the analysis channels at dynamically varying distances from a centerpoint of the scanning device. As a fourth step, molecular samples are loaded into the analysis channels with a robot.

19 Claims, 3 Drawing Sheets

SYSTEM AND METHOD FOR CHROMATOGRAPHY AND ELECTROPHORESIS USING CIRCULAR OPTICAL SCANNING

CROSS-REFERENCE TO RELATED APPLICATIONS

The terminal portion of any patent granted on the subject application beyond the expiration date of U.S. Pat. No. 6,100,535 is disclaimed. U.S. Pat. No. 6,100,535 for "Rotary Confocal Scanner for Detection of Capillary Arrays" by Mathies et al, assigned to The Regents of the University of California, which is the same assignee as the present application, issued Aug. 8, 2000 from an application filed Jan. 29, 1998. The specification and drawings of U.S. Pat. No. 6,100,535 are incorporated herein in their entirety by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates generally to systems and methods applicable to chromatography and electrophoresis, and more particularly to a system and method for chromatography and electrophoresis using circular optical scanning.

2. Discussion of Background Art

Chromatography is a technique for separating molecules based on how they tend to cling to or dissolve in various solids, liquids and gases. Electrophoresis is also a technique for separating large molecules (such as DNA fragments or proteins) from a mixture of similar molecules. However, in electrophoresis, an electric current is passed through a medium containing the molecules. Each type of molecule travels through the medium at a different rate, depending on its electrical charge and size, which creates a series of identifying bands.

Many chromatography and electrophoresis systems, having multiple analysis columns within a microchannel plate, use scanning optical detection systems based on Laser Induced Fluorescence (LIF) or UV absorbence to detect the presence of analytes as they travel past the scan path of an optical detection beam. These scanning detection systems typically include a high intensity light source (e.g. laser), one or more optical detectors (e.g. Photo-Multiplier Tubes (PMTs) or Charge Coupled Devices (CCDs), various electronic circuits (e.g. amplifiers, filters, A-to-D converters), and a computer for control, data collection, and storage.

FIG. 1 is a block diagram of a prior art 100 system using "linear" optical scanning. The prior art optical scanning systems 100 use linear scan motors to move the light source back and forth in a straight line 102 across the analysis columns in the microchannel plate so as to periodically excite and detect the presence of analyte molecules. The number of analysis columns that can be detected in these linear scanned systems is limited principally by the width of the array of columns, the velocity of the analytes as they move past the detecting light beam, the intensity of the illuminating light beam on the analyte, and the spatial resolution, accuracy, and maximum speed with which the linear scan stage can be driven (usually via an electric motor). High resolution, accuracy and low vibration requirements limit current stepper motors and servo motors limit the maximum velocities of linear scan stages to approximately 30 cm/sec and therefore, limit the number of analysis columns that can be detected to approximately 100 analysis columns maximum. This is because for wider microchannel plates, some of the analyte molecules on one end of the microchannel plate may pass through the linear detection area before the linear detector can return to the analysis columns in which they are contained.

Recently, efforts are being made to sequence all the molecules in the human genome as soon as possible. Due to this and other growing needs for even faster chromatography and electrophoresis systems, linear systems limited to only 100 analysis columns are too constricting.

In response to the concerns discussed above, what is needed is a system and method for chromatography and electrophoresis that overcomes the problems of the prior art.

SUMMARY OF THE INVENTION

The present invention is a system and method for chromatography and electrophoresis using circular optical scanning. Within the system of the present invention there are either one or more rectangular microchannel plates or radial microchannel plates. Each microchannel plate has a set of analysis channels for insertion of molecular samples for analysis. One or more scanning devices repeatedly pass over the analysis channels in one direction at a predetermined rotational velocity and with a predetermined rotational radius. Radial microchannel plates are built from a substrate whose first analysis channel has a first longitudinal axis, and whose next analysis channel has another longitudinal axis disposed at a non-parallel angle with respect to the first longitudinal axis.

In another aspect of the invention, each microchannel plate could have hundreds or thousands of analysis channels to increase system throughput.

In another aspect of the invention, the rotational radius may be dynamically varied so as to monitor the molecular sample at various positions along a analysis channel. Sample loading robots may also be used to input molecular samples into the analysis channels within one or more microchannel plates.

The method of the present invention includes the steps of accessing a microchannel plate, having a set of analysis channels, and passing a scanning device repeatedly over the analysis channels in a constant direction.

In another aspect of the invention, the method further includes the steps of, selecting a second microchannel plate, having analysis channels, and passing the scanning device repeatedly from the first microchannel plate to the second microchannel plate is a constant direction. Alternatively, the accessing steps are replaced with the step of accessing a radial microchannel plate, having neighboring analysis channels positioned at non-parallel angle with respect to each other.

In another aspect of the invention, the method further includes the step of, passing the scanning device over the analysis channels at a dynamically varying distance from a centerpoint of the scanning device.

In another aspect of the invention, the method further includes the step of, loading molecular samples into the analysis channels with a robot.

The system and method of the present invention are particularly advantageous over the prior art because a circular scanned optical detection system is disclosed that enables efficient detection of material samples being analyzed by multiple chromatography or electrophoresis units each containing a set of analysis channels. This system enables at least a quadrupling of a number of chromatography or electrophoresis sample analysis channels that can be detected by a single optical detection system and can result in a significant cost savings, simpler scanning hardware, and reduced laboratory space needed for high volume material analysis systems based on chromatography or electrophoresis. Also disclosed is a concept for building electrophoresis instrument modules or clusters that have thousand of electrophoresis analysis channels and efficiently share a limited number of circular scanning devices and sample loading robots.

Furthermore, the present invention is applicable to chromatography and electrophoresis material analysis applications involving optical detection, including those which analyze organic and inorganic materials. Well recognized applications include DNA fragment sizing, DNA sequencing, analysis of biological materials for drug discovery effects, and genetic disease susceptibility diagnostics and studies.

These and other aspects of the invention will be recognized by those skilled in the art upon review of the detailed description, drawings, and claims set forth below.

DETAILED DESCRIPTION OF THE PREFERRED EMBODIMENT

Figure 2:
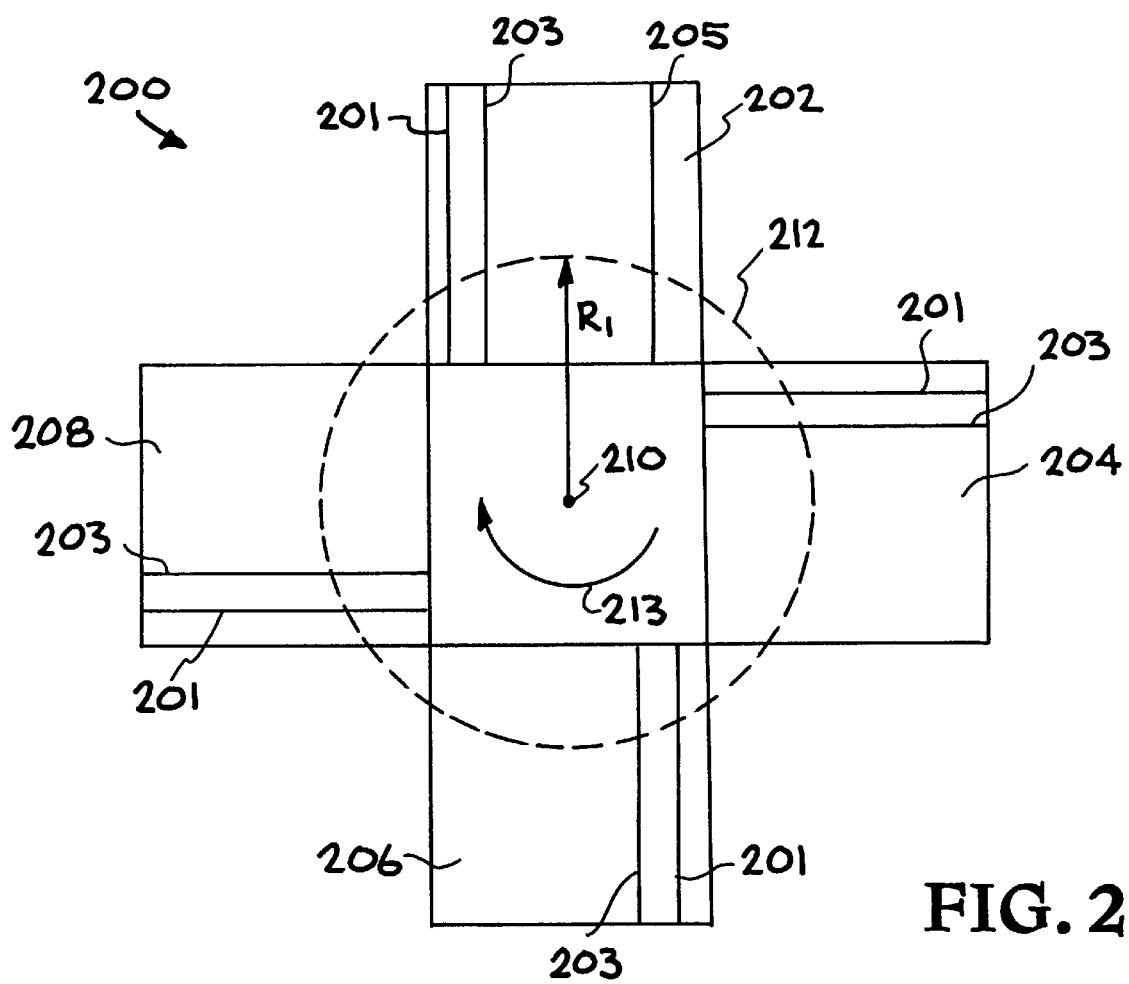
FIG. 2 is a block diagram of a system for chromatography and electrophoresis using "circular" optical scanning according to one embodiment of the present invention.

FIG. 2 is a block diagram of a system 200 for chromatography and electrophoresis using "circular" optical scanning according to one embodiment of the present invention. The system 200 includes four microchannel plates 202, 204, 206, and 208. Each microchannel plate is of a standard type which is rectangular in shape and has a first analysis channel 201, a second analysis channel 203, up through an "nth" analysis channel 205, where "n" is any integer. Each plate is positioned approximately perpendicular with respect to each neighboring plate; however, those skilled in the art will recognize that the plates can be positioned at many different angles with respect to each other.

Figure 1:
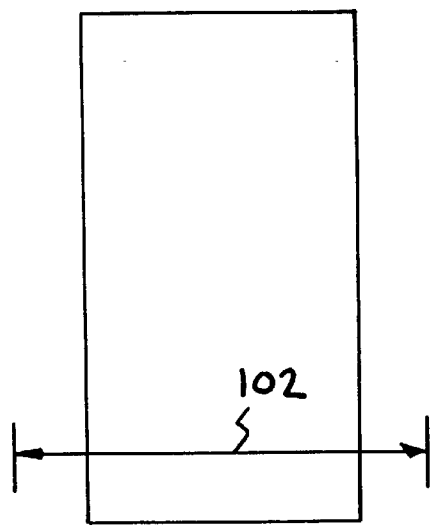
FIG. 1 is a block diagram of a prior art system using "linear" optical scanning.

A scanning device 210, having a center point (a.k.a. a center axis), is located between the four microchannel plates. The scanning device 210 is a standard type of scanning device that is well known in the art. For example, a scanning system that may be used as scanning device 210, is described in U.S. Pat. No. 5,274,240, dated Dec. 28, 1993, to Richard A Mathies, Xiaohua C. Huang, and Mark A. Quesada, the disclosure, including the drawings, of which is incorporated herein by reference. The drawings of U.S. Pat. No. 5,274,240, particularly FIG. 1, show a confocal-fluorescence capillary array scanner.

The scanning system in U.S. Pat. No. 5,274,240 is described at column 4, beginning at line 37 and ending at column, line 14 as follows: "A confocal fluorescence detection system for use with capillary arrays is shown in FIG. 1. An argon ion laser (Model 2020, Spectra-Physics, Mountain View, Calif.), not shown, is used as the excitation source. The laser beam is expanded to 5 mm diameter, collimated, and then directed through a 32×, N.A. 0.4 infinite conjugate objective 11 (LD Plan—chromat 440850, Carl Zeiss, West Germany) by a long-pass dichroic beamsplitter 12 (480 DM, Omega Optical, Brattleboro, Vt.). The dichroic beam splitter 12 reflects the excitation laser beam into the objective 11 but transmits fluorescent light collected byte objective which is Stokes shifted to longer wavelengths. The objective focuses the exciting laser on the sample and gathers the fluorescence with very high collection efficiency. The use of an infinite conjugate objective permits vertical adjustment of the probe volume by translating the objective with the mount 13 secured to the base 14 with no significant perturbation of the optical alignment. The focused 1 mW, 488 nm wavelength beam is focused to a 10 µm beam diameter and a 25 µm confocal beam parameter. The fluorescence emission is passed back through the long-pass dichroic beam splitter 12 mounted on the base 14 to reduce laser interference and to separate the excitation and detection paths. The fluorescence is then focused by a 75 mm focal length lens 16 mounted on the base 14 onto a 400 µm pinhole which serves as the confocal spatial filter. The light passing through the pinhole is filtered by a 488 nm rejection band filter (488 RB filter, Omega Optical, Brattleboro, Vt.), a long-pass cutoff filter (Schott GG-495, Esco, Oakridge, N.J.), a bandpass fluorescence filter (530 DF60, Omega Optical, Brattleboro, Vt.), all mounted within the housing 17, followed by detection with a cooled photomultiplier tube 18 (RCA 31034A, Burle Industries, Lancaster, Pa.). The spatial filter, the optical filters and photomultiplier tube are mounted on base 14. The output of the phototube is amplified and filtered with a low-noise amplifier (SR560, Standford Research Systems, Sunnyvale, Calif.), digitized with a 12 bit analog-to-digital board (DASH-16 F, metra-Byte, Taunton, Mass.) and stored in an IBM PS/2 microcomputer. The electronic filter used for the phototube output was a first-order, active, low-pass filter (DC to 400 Hz) with a 12 dB/octave rolloff.

Other examples of scanning systems that may be used as scanning device 210 are described in U.S. Pat. No. 5,483,075, dated Jan. 9, 1996, to Douglas H. Smith and Charles R. Connnell, assigned to Perkin-Elmer Corporation, for a Rotary Scanning Apparatus, U.S. Pat. No. 5,884,239, dated Mar. 16, 1999, to Carl J. Romanik, Jr., for an optical system for accurate monitoring of the position and orientation of an object; and U.S. Pat. No. 5,877,883, patented Mar. 2, 1999, by Inoue et. al., for an optical scanner. An optical focal plane of the scanning device 210 is preferably parallel to the analysis channels and in a same plane as of the analysis channels. The scanning device 210 excites and detects a presence of analyte molecules passing within analysis channels in the microchannel plates along a scanning circle 212 of radius R1, from the center point of the scanning device 210, using a simple constant velocity rotating motor rotating in a direction shown 213. The radius R1 can be variable and dynamically adjusted during analysis into various elliptically varying patterns. The scanning device 210 rotates from the first analysis channel 201 to the second analysis channel 203 of each microchannel plate. During analysis, the scanning device 210 rotates repeatedly in only one direction from the first analysis channel 201 to the second analysis channel 203. However, those skilled in the art will recognize that the scanning device 210 can also rotate repeatedly in an opposite direction during analysis.

While the plates 202, 204, 206, and 208 in FIG. 2 are shown within a single geometric plane, in alternate embodiments, one or more of the plates can be positioned at any angle with respect to the scanning device 210 or in a multi-level platter arrangement. However, in a simplest embodiment, only one microchannel plate need be positioned at any angle with respect to the scanning device 210.

This circular scanning system is a much simpler than linear scanning systems which must reverse their direction at an end of each scan. Linear scanning requires a much more complex motor control system than circular scanning in order to maintain constant velocities over the analysis channels, Circular scanning systems also require much less control circuitry and more simple data reconstruction algorithms.

The circular scanning system maintains a constant scan velocity across, all analysis columns so that detected signals from all analysis columns have an equal time duration. Equal time duration is important for maintaining uniform signal sensitivity from all analysis columns and for producing a more periodic signal that simplifies data analysis (e.g. base calling). In contrast linear scanning systems have difficulty maintaining uniform scan velocities because of their constant change of directions and associated accelerations. Non-uniform scan velocities result in uneven times between samples for all electrophoresis columns except those near a center of the microchannel plate.

With circular scanning, as the number of analysis channels is increased, an energy source power used to excite the molecules within the channels is adjusted to maintain an adequate signal to noise ratio (S/N) depending upon how many channels are being scanned and a scan velocity of the scanning motor.

In a special case of DNA sequencing, the scanning device 210 is preferably configured as a confocal optical detection system using a laser and a multi-spectral detector, consisting of four dichroic filters, four bandpass filters, and four photo-multiplier tubes (PMTs). In this case the confocal optics are located on a rotating circular platform connected to a shaft that is driven by the constant velocity motor. The laser, multi-spectral detector and a set of steering optics are mounted on a stationary surface. The PMTs may be replaced with CCDs, Avalanche PhotoDiodes (APDs), or other similar devices.

Figure 3:
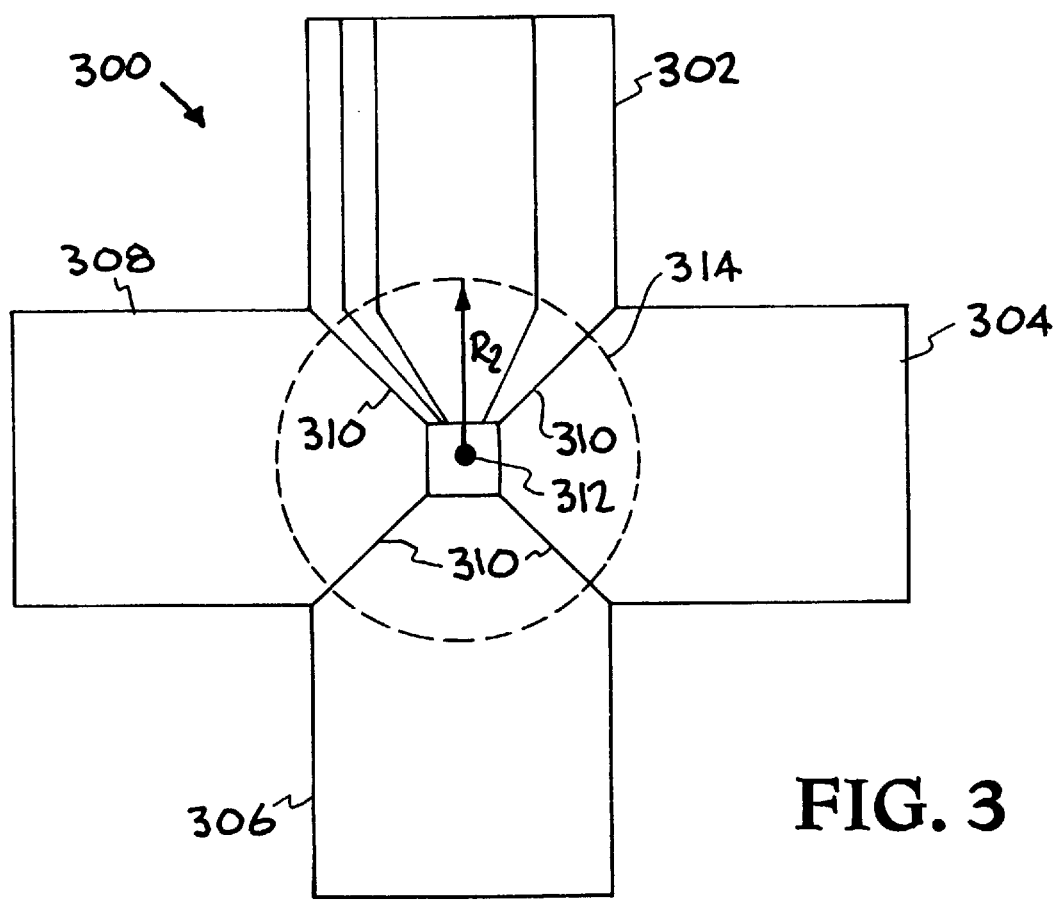
FIG. 3 is a block diagram of a system for chromatography and electrophoresis using circular optical scanning according to a second embodiment of the present invention.

FIG. 3 is a block diagram of a system 300 for chromatography and electrophoresis using circular optical scanning according to a second embodiment of the present invention. This system 300 includes four microchannel plates 302, 304, 306, and 308 like system 200, however, these plates 302, 304, 306, and 308 each have a taper 310. The taper 310 permits a scanning device 312 that is located at an approximate center point of the four microchannel plates to have a scanning circle 314 of radius R2, which is less than the scanning circle 212 of system 200. The scanning system 200 is a standard type of scanning device that is well known in the art. The scanning system 200 may be the systems described in U.S. Pat. Nos. 5,274,240; 5,483,075; 5,884, 239; or 5,877,883 as set out above in connection with scanning device 210. A smaller scanning circle allows either a velocity of a scanning motor to be decreased or permits analysis of a greater number of analysis channels within a given time period.

Figure 4:
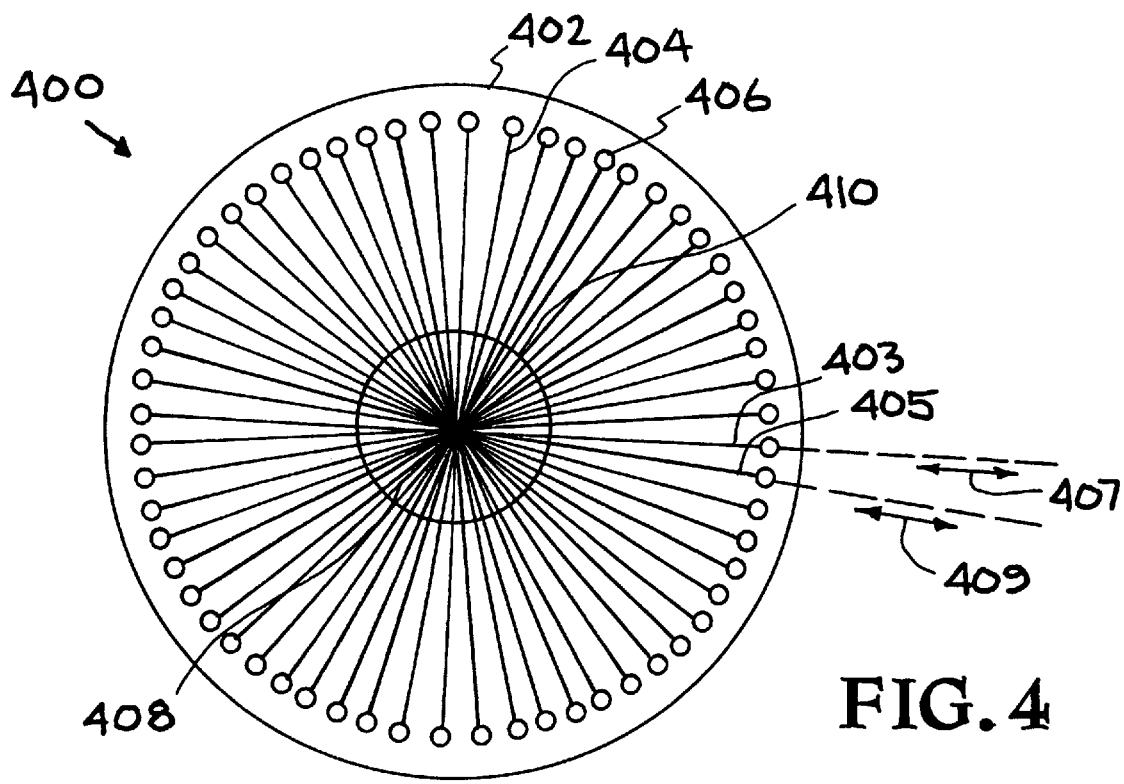
FIG. 4 is a block diagram of a system for chromatography and electrophoresis using circular optical scanning according to a third embodiment of the present invention.

FIG. 4 is a block diagram of a system 400 for chromatography and electrophoresis using circular optical scanning according to a third embodiment of the present invention. This system 400 includes a single radial microchannel plate 402 substrate. The radial plate 402 has a set of analysis channels 404, each having a sample loading well 406. The analysis channels 404 are oriented such that a longitudinal axis 407 of a first analysis channel 403 is positioned at a non-parallel angle with respect to a longitudinal axis 409 of a next analysis channel 405. A scanning device 408 is located at an approximate center point of the radial plate and has a one directional scanning circle 410 of radius R3. The scanning system 408 is a standard type of scanning device that is well known in the art. The scanning system 408 may be the systems described in U.S. Pat. Nos. 5,274,240; 5,483,075; 5,884,239; or 5,877,883 as set out above in connection with scanning device 210. An important feature of the radial plate design is that the scanning circle 410 radius can be dynamically varied during a single chromatography or electrophoresis analysis run. This permits detection of molecules as they separate at various distances from an injection point. Thus various separations requiring longer or shorter lengths can be performed on the same system. The radial plate design also permits study of the electrophoresis/chromatography process for any given separation media and sample combination.

Figure 5:
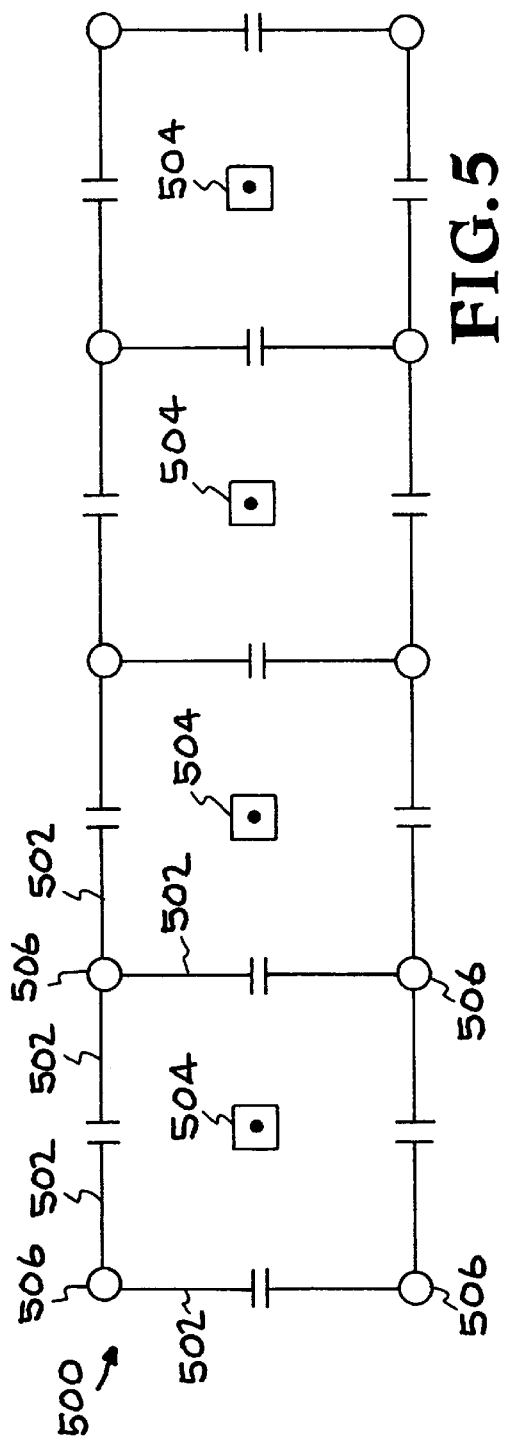
FIG. 5 is a block diagram of a first system for chromatography and electrophoresis using multiple circular optical scanning stations.

FIG. 5 is a block diagram of a first system 500 for chromatography and electrophoresis using multiple circular optical scanning stations. The first system 500 includes a set of microchannel plates 502, a set of sample loading robots 504, and a set of scanning devices 506 configured as shown. The scanning devices 506 are standard types of scanning devices that are well known in the art. The scanning devices 506 may be the systems described in U.S. Pat. Nos. 5,274, 240; 5,483,075; 5,884,239; or 5,877,883 as set out above in connection with scanning device 210. Those skilled in the art will know that many other configurations are also possible for the first system 500, some of which may use a different number of robots 504.

In one exemplary configuration, the first system 500 is organized into four modules with eight plates arranged in a square pattern in each module. One multi-axis robot system feeds samples to all plates in its square. Plates common to two squares are handled by either robot. Typically, each robot will service about three plates. For electrophoresis capillaries or microchannels having typical lengths of 50 cm, the first system 500 would occupy a footprint measuring less than 2 meters×8 meters. For a DNA sequencing system that uses electrophoresis plates having 384 microchannels/capillaries, sequencing throughput for the first system 500 would be approximately 3.7 billion bases per year for single shift operation during 250 days per year. Principal performance assumptions for such estimates are that each channel can resolve 500 bases and that a run cycle time is three hours.

Figure 6:
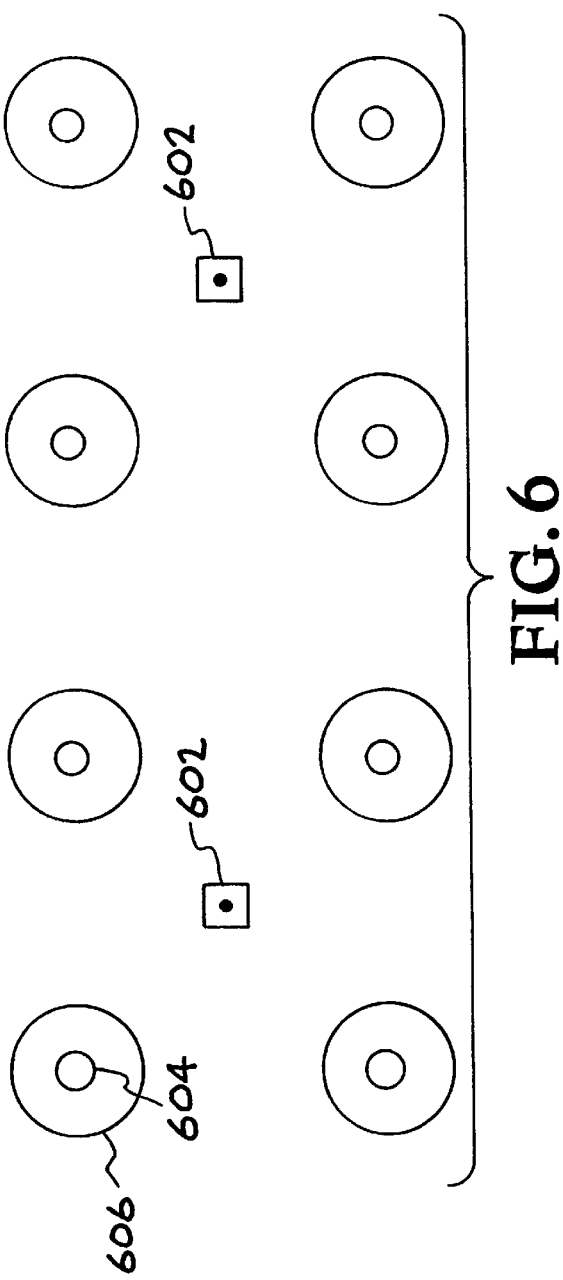
FIG. 6 is a block diagram of a second system for chromatography and electrophoresis using multiple circular optical scanning stations.

FIG. 6 is a block diagram of a second system 600 for chromatography and electrophoresis using multiple circular optical scanning stations. The second system 600 includes a set of sample loading robots 602, a set of scanning devices 604, and a set of radial microchannel plates 606 configured as shown. The scanning devices 604 are standard types of scanning devices that are well known in the art. The scanning devices 604 may be the systems described in U.S. Pat. Nos. 5,274,240; 5,483,075; 5,884,239; or 5,877,883 as set out above in connection with scanning device 210. Those skilled in the art will know that many other configurations are also possible for the second system 600, some of which may use a different number of robots 602.

While the present invention has been described with reference to a preferred embodiment, those skilled in the art will recognize that various modifications may be made. Variations upon and modifications to the preferred embodiment are provided by the present invention, which is limited only by the following claims.

What is claimed is:

1. A method of scanning in chromatography and electrophoresis comprising the steps of:
   providing a first microchannel plate,
   providing a first microchannel plate first analysis channel on said first microchannel plate,
   providing a first microchannel plate second analysis channel on said first microchannel plate,
   providing a second microchannel plate,
   providing a second microchannel plate first analysis channel on said second microchannel plate,
   providing a second microchannel plate second analysis channel on said second microchannel plate,
   positioning said first microchannel plate and said second microchannel plate at an angle relative to each other, and
   scanning from said first microchannel plate to said second microchannel plate along a scanning circle.

2. The method of claim 1 further comprising the steps of repeatedly scanning from said first microchannel plate to said second microchannel plate along said scanning circle.

3. The method of claim 2 wherein said steps of repeatedly scanning from said first microchannel plate to said second microchannel plate along said scanning circle are conducted only in one direction around said scanning circle.

4. The method of claim 1 wherein said first microchannel plate and said second microchannel plate are positioned perpendicular to each other.

5. The method of claim 1 wherein said step of scanning includes scanning from said first microchannel plate first analysis channel to said first microchannel plate second analysis channel along said scanning circle.

6. The method of claim 1 wherein said step of scanning includes scanning from said first microchannel plate second analysis channel to said second microchannel plate first analysis channel along said scanning circle.

7. The method of claim 6 wherein said step of scanning includes scanning from said second microchannel first analysis channel to said second microchannel plate second analysis channel along said scanning circle.

8. The method of claim 1 wherein said step of scanning includes scanning from said first microchannel plate first analysis channel to said first microchannel plate second analysis channel to said second microchannel plate first analysis channel to said second microchannel plate second analysis channel along said scanning circle.

9. The method of claim 8 further comprising the steps of repeatedly scanning from said first microchannel plate first analysis channel to said first microchannel plate second analysis channel to said second microchannel plate first analysis channel to said second microchannel plate second analysis channel along said scanning circle.

10. The method of claim 9 wherein said steps of repeatedly scanning from said first microchannel plate first analysis channel to said first microchannel plate second analysis channel to said second microchannel plate first analysis channel to said second microchannel plate second analysis channel along said scanning circle are conducted only in one direction around said scanning circle.

11. The method of claim 10 said first microchannel plate and said second microchannel plate are positioned perpendicular to each other.

12. The method of claim 11 wherein said scanning step includes locating a central point between said first microchannel plate and said second microchannel plate, and creating said scanning circle by utilizing a fixed radius from said central point.

13. The method of claim 1 wherein said scanning step includes locating a central point between said first microchannel plate and said second microchannel plate, and creating said scanning circle by utilizing a variable radius from said central point.

14. The method of claim 1 further comprising the steps of providing additional analysis channels on said first microchannel plate up through an "nth" analysis, where "n" is any integer above 2 and providing additional analysis channels on said microchannel plate up through an "nth" analysis channel, where "n" is any integer above 2.

15. The method of claim 14 wherein the steps of scanning include scanning from said first microchannel plate first analysis channel to said first microchannel plate second analysis channel and from the first channel plate second analysis channel to said additional analysis channels on said first microchannel plate along said scanning circle.

16. The method of claim 14 wherein the steps of scanning include scanning from said second microchannel plate first analysis channel to said second microchannel plate second analysis channel and from said second microchannel plate second analysis channel to said additional analysis channels on said second microchannel plate along said scanning circle.

17. The method of claim 1 said scanning step includes scanning from said first microchannel plate to said second microchannel plate at a constant velocity along said scanning circle.

18. The method of claim 1 further comprising the steps of repeatedly scanning said first microchannel plate first analysis channel to said first microchannel plate second analysis channel at a constant velocity along said scanning circle.

19. A method of scanning in chromatography and electrophoresis, comprising the steps of:
   providing a first Microchannel plate,
   providing a first microchannel plate first analysis channel on said first microchannel plate,
   providing a first microchannel plate second analysis channel on said first microchannel plate,
   providing a second microchannel plate,
   providing a second microchannel plate first analysis channel on said second microchannel plate,
   providing a second microchannel plate second analysis channel on said second microchannel plate,
   providing a third microchannel plate,
   providing a third microchannel plate first analysis channel on said third microchannel plate,
   providing a third microchannel plate second analysis channel on said third microchannel plate,
   providing a fourth microchannel plate,
   providing a fourth microchannel plate first analysis channel on said fourth microchannel plate,
   providing a fourth microchannel plate second analysis channel on said fourth microchannel plate, positioning said second microchannel plate perpendicular to said first microchannel plate, positioning a third microchannel plate perpendicular to said second microchannel plate, positioning a fourth microchannel plate perpendicular to said third microchannel plate and perpendicular to said first microchannel plate, locating a central point between said first microchannel plate, said second microchannel plate, said third microchannel plate, and said fourth microchannel plate, creating a scanning circle by utilizing a radius from said central point, and scanning from said first microchannel plate first analysis channel to said first microchannel plate second analysis channel to said second microchannel plate first analysis channel to said second microchannel plate second analysis channel to said third microchannel plate first analysis channel to said third microchannel plate second analysis channel to said fourth microchannel plate first analysis channel to said fourth microchannel plate second analysis channel at a constant velocity along said scanning circle.

* * * * *